United States Patent
Sakuraoka et al.

(10) Patent No.: US 7,998,326 B2
(45) Date of Patent: Aug. 16, 2011

(54) ION SENSOR, ION SENSOR MODULE, AND ION SENSOR MANUFACTURING METHOD

(75) Inventors: Masayuki Sakuraoka, Otawara (JP); Sonoe Suzuki, Otawara (JP); Takehiko Onuma, Oyama (JP); Emiko Tamura, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 138 days.

(21) Appl. No.: 11/950,632

(22) Filed: Dec. 5, 2007

(65) Prior Publication Data

US 2008/0135409 A1 Jun. 12, 2008

(30) Foreign Application Priority Data

Dec. 6, 2006 (JP) ................. 2006-329357

(51) Int. Cl.
*G01N 27/26* (2006.01)
*G01N 27/403* (2006.01)
*G01N 27/333* (2006.01)
*G01N 33/49* (2006.01)
*G01N 33/493* (2006.01)

(52) U.S. Cl. ............. 204/416; 204/403.01; 204/409; 204/435

(58) Field of Classification Search .......... 204/400–435; 205/775–792
See application file for complete search history.

(56) References Cited

U.S. PATENT DOCUMENTS

| 4,758,325 | A | * | 7/1988 | Kanno et al. ............ 204/411 |
| 4,797,192 | A | | 1/1989 | Takiguchi |
| 4,874,499 | A | * | 10/1989 | Smith et al. ............ 204/403.03 |
| 4,935,117 | A | * | 6/1990 | Uematsu et al. ............ 204/411 |
| 5,505,836 | A | | 4/1996 | Miyahara et al. |
| 5,846,392 | A | * | 12/1998 | Knoll ............ 205/778 |
| 6,110,338 | A | * | 8/2000 | Rokugawa ............ 204/418 |
| 6,322,680 | B1 | * | 11/2001 | Itsygin ............ 204/416 |
| 6,423,197 | B1 | * | 7/2002 | Lenferink et al. ............ 204/408 |
| 6,689,272 | B2 | * | 2/2004 | Meruva et al. ............ 205/787 |
| 2005/0253061 | A1 | * | 11/2005 | Cameron et al. ............ 250/287 |

FOREIGN PATENT DOCUMENTS

| JP | 11-295261 | 10/1999 |
| JP | 3111283 | 9/2000 |

* cited by examiner

*Primary Examiner* — Alexa D Neckel
*Assistant Examiner* — Jennifer Dieterle
(74) *Attorney, Agent, or Firm* — Oblon, Spivak, McClelland, Maier & Neustadt, L.L.P.

(57) ABSTRACT

An ion sensor includes a sensor main body having a channel for a sample and an opening connected to the channel, a responsive portion which is filled in the opening and selectively responds to a specific ion, an electrode which has a ring shape, is set such that a central axis of the ring is substantially perpendicular to a central axis of the channel, and senses the response, and an output terminal which is formed out of one metal plate out of which the electrode is formed, has a pin shape, and is held by the sensor main body such that an axis extends along a direction substantially perpendicular to the central axis of the channel and the central axis of the ring.

4 Claims, 8 Drawing Sheets

ION SENSOR, ION SENSOR MODULE, AND ION SENSOR MANUFACTURING METHOD

CROSS-REFERENCE TO RELATED APPLICATIONS

This application is based upon and claims the benefit of priority from prior Japanese Patent Application No. 2006-329357, filed Dec. 6, 2006, the entire contents of which are incorporated herein by reference.

BACKGROUND OF THE INVENTION

1. Field of the Invention

The present invention relates to an ion sensor and ion sensor module used to analyze ions contained in a liquid, and a method of manufacturing the ion sensor and, more particularly, to an ion sensor and ion sensor module for analyzing ions contained in human blood or urine, and a method of manufacturing the ion sensor.

2. Description of the Related Art

An ion sensor module calculates the concentrations of electrolytes such as sodium ions, potassium ions, and chlorine ions contained in a sample. The ion sensor module has an ion sensor that senses the potential corresponding to each electrolyte, and a reference electrode device that senses a predetermined potential as the basis of the potential sensed by the ion sensor. The concentration of the electrolyte is calculated on the basis of the potentials sensed by the ion sensor and reference electrode device. The ion sensor and reference electrode device are used as they are attached to an automatic analyzer for analyzing components contained in a sample as objects of biochemistry test items or immunity test items or to an apparatus for exclusively measuring electrolytes.

The ion sensor senses the potential of a responsive portion made of components containing a responsive material which selectively responds to specific ions contained in a sample. The reference electrode device senses a predetermined potential generated with respect to the sample. The concentration of the specific ions is calculated by measuring the electromotive force as a potential difference between the ion sensor and reference electrode device.

As a method of manufacturing an ion sensor that can be made compact, there is a known method that forms a responsive portion by repetitively coating an ion sensor with a small amount of a solution in which a responsive material that responds to ions to be measured is dissolved, and thoroughly drying the solution (e.g., Jpn. Pat. Appln. KOKAI Publication No. 11-295261).

In some cases, however, an air bubble is formed in the coated solution, and this air bubble forms a pore in the responsive portion after the solution is dried. If this pore is formed in the surface of the responsive portion that comes in contact with a sample, a preceding sample remains in the pore and contaminates a sample to be measured next when testing, e.g., a plurality of samples different in concentration, thereby adversely affecting the measurement results. This decreases the yield of ion sensors.

BRIEF SUMMARY OF THE INVENTION

It is an object of the present invention to provide an ion sensor having a high yield, an ion sensor module, and a method of manufacturing the ion sensor.

According to the first aspect of the present invention, there is provided an ion sensor comprising: a sensor main body having a channel for a sample and an opening connected to the channel; a responsive portion which is filled in the opening and selectively responds to a specific ion; an electrode which has a ring shape, is set such that a central axis of the ring is substantially perpendicular to a central axis of the channel, and senses the response; and an output terminal which is formed out of one metal plate out of which the electrode, has a pin shape, and is held by the sensor main body such that an axis extends along a direction substantially perpendicular to the central axis of the channel and the central axis of the ring.

According to the second aspect of the present invention, there is provided an ion sensor comprising: a sensor main body having a channel for a sample and an opening connected to the channel; a responsive portion which is filled in the opening and selectively responds to a specific ion; an electrode which is embedded in the sensor main body such that the electrode is partially brought into contact with the responsive portion, and senses the response; and an output terminal which is held by the sensor main body, and outputs the sensed response to an external apparatus.

According to the third aspect of the present invention, there is provided an ion sensor module comprising: an ion sensor cited in the first aspect of the present invention; a reference electrode device having a reference electrode main body having a channel for the sample, a liquid junction hole formed in the channel of the reference electrode main body, an internal liquid contained in the reference electrode main body such that the internal liquid is adapted to communicate with the sample through the liquid junction hole, and an output terminal which is partially brought into contact with the internal liquid and outputs a substantially constant potential in the liquid junction hole; and a container which detachably clamps the ion sensor and the reference electrode device to connect the channel of the sensor main body and the channel of the reference electrode device.

According to the forth aspect of the present invention, there is provided an ion sensor module comprising: an ion sensor cited in the second aspect of the present invention; a reference electrode device having a reference electrode main body having a channel for the sample, a liquid junction hole formed in the channel of the reference electrode main body, an internal liquid contained in the reference electrode main body such that the internal liquid is adapted to communicate with the sample through the liquid junction hole, and an output terminal which is partially brought into contact with the internal liquid and outputs a substantially constant potential in the liquid junction hole; and a container which detachably clamps the ion sensor and the reference electrode device to connect the channel of the sensor main body and the channel of the reference electrode device.

According to the fifth aspect of the present invention there is provided an sensor manufacturing method comprising: inserting a pin into a channel for a sample formed in a sensor main body; coating the inserted pin and a wall surface of an opening connected to the channel with a solution prepared by dissolving, in a solvent, a responsive material which selectively responds to a specific ion, such that the opening is filled with the solution; and removing the pin from the channel after the solvent in the coated solution has evaporated.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the generation description given above and the detailed description of the embodiments given below, serve to explain the principles of the invention.

DETAILED DESCRIPTION OF THE INVENTION

An embodiment of an ion sensor module according to the present invention will be explained below with reference to FIGS. 1 to 14.

Figure 1:
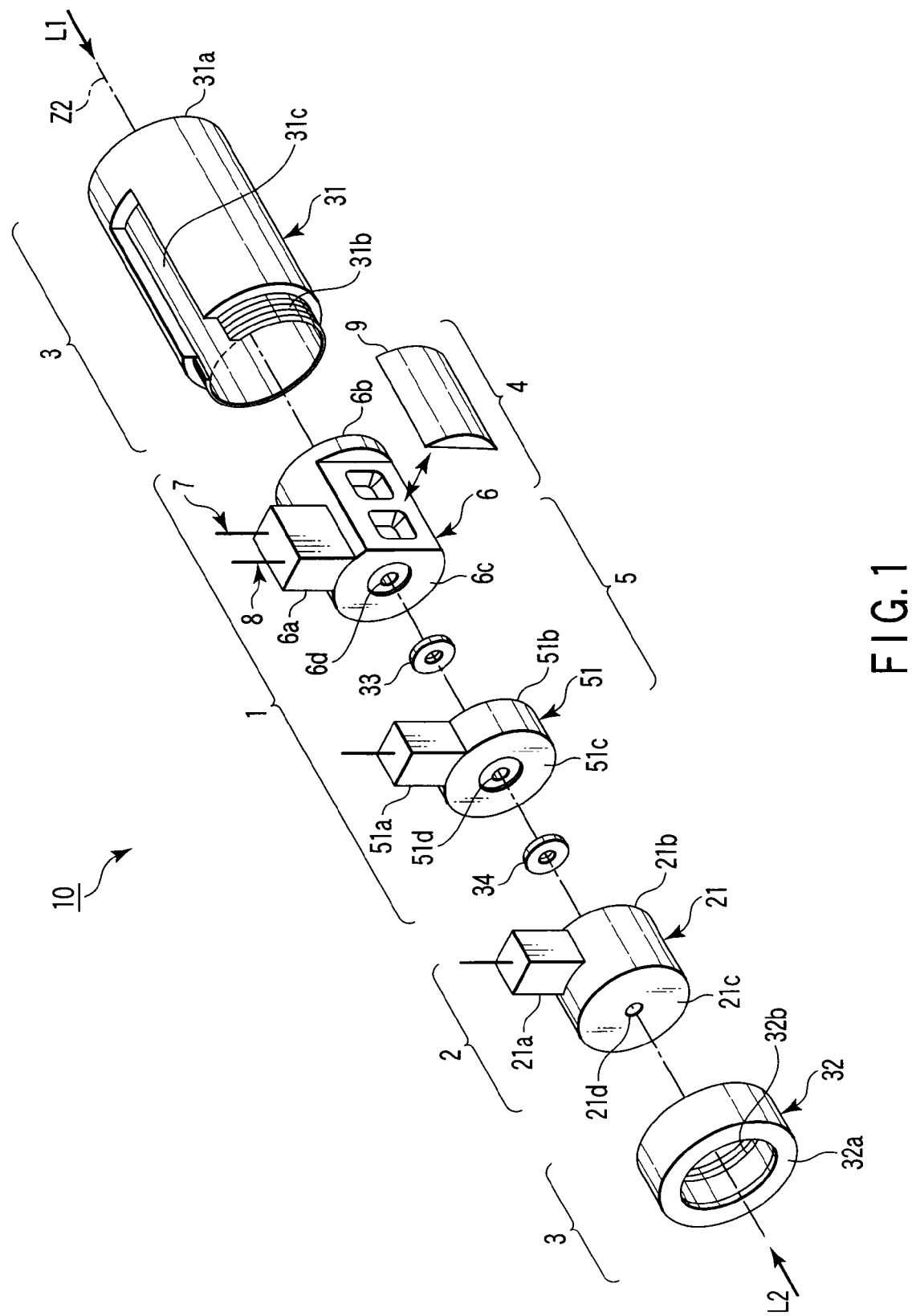
FIG. 1 is a view showing the arrangement of an ion sensor module according to an embodiment of the present invention.

FIG. 1 is a view showing the arrangement of the ion sensor module according to the embodiment of the present invention. An ion sensor module 10 comprises an ion sensor unit 1 including a plurality of ion sensors that selectively respond to specific ions such as sodium ions, potassium ions, and chlorine ions contained in a sample, a reference electrode device 2 as the basis of electrodes of the ion sensor unit 1, and a container 3 that accommodates the ion sensor unit 1 and reference electrode device 2.

The ion sensor unit 1 has a multi-ion sensor 4 including first and second ion sensors manufactured in the first manufacturing step, and a third ion sensor 5 manufactured in the second manufacturing step different from the first manufacturing step. The multi-ion sensor 4 has a first sensor main body 6, first ion sensor 7, second ion sensor 8, and cover 9.

Figure 2:
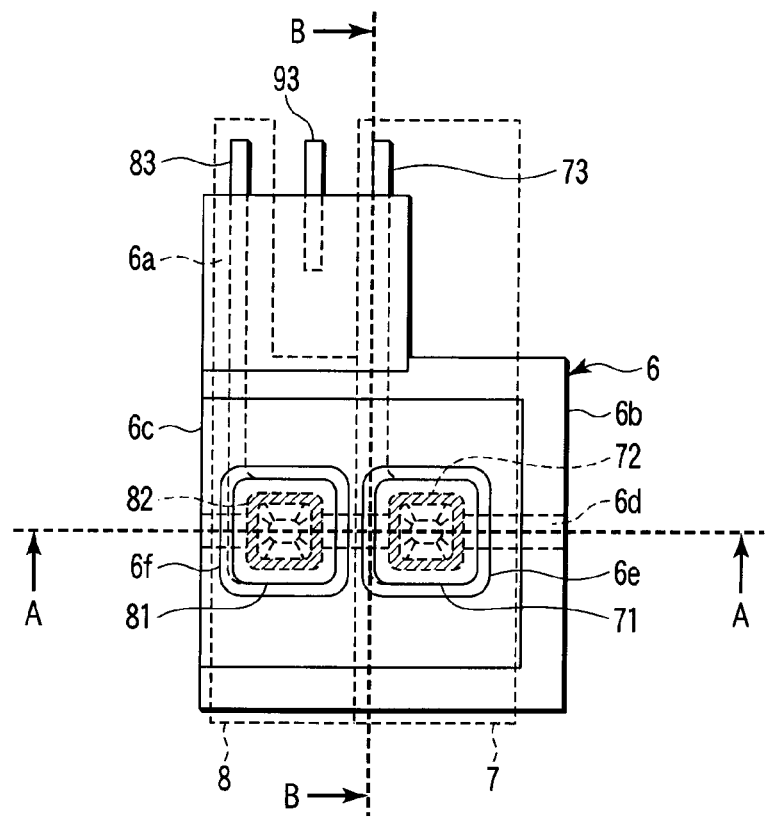
FIG. 2 is a view showing the side surface of a multi-ion sensor shown in FIG. 1.
Figure 3:
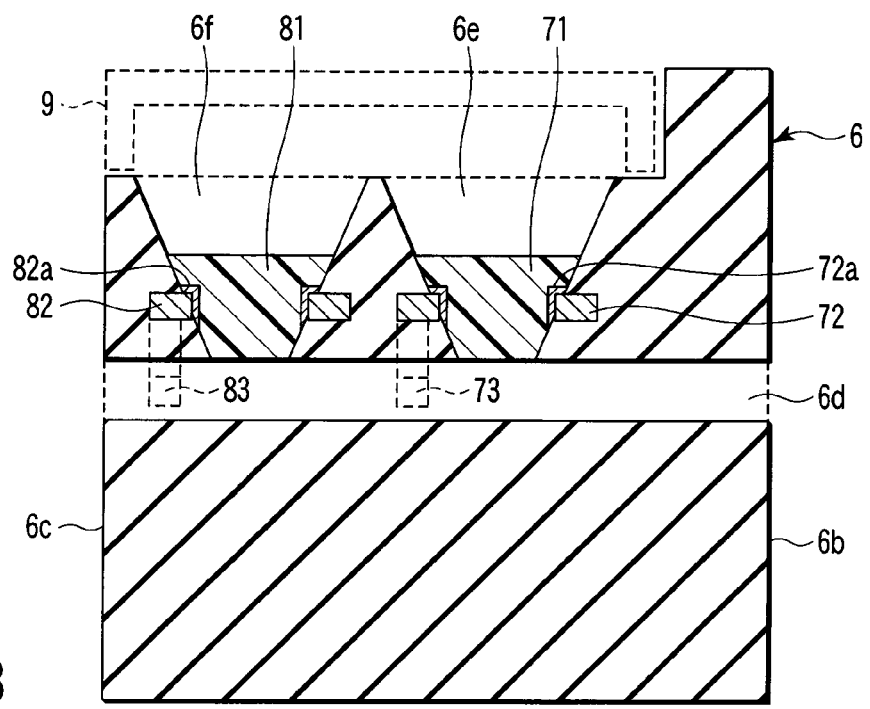
FIG. 3 is a view showing the A-A section of the multi-ion sensor shown in FIG. 2.
Figure 4:
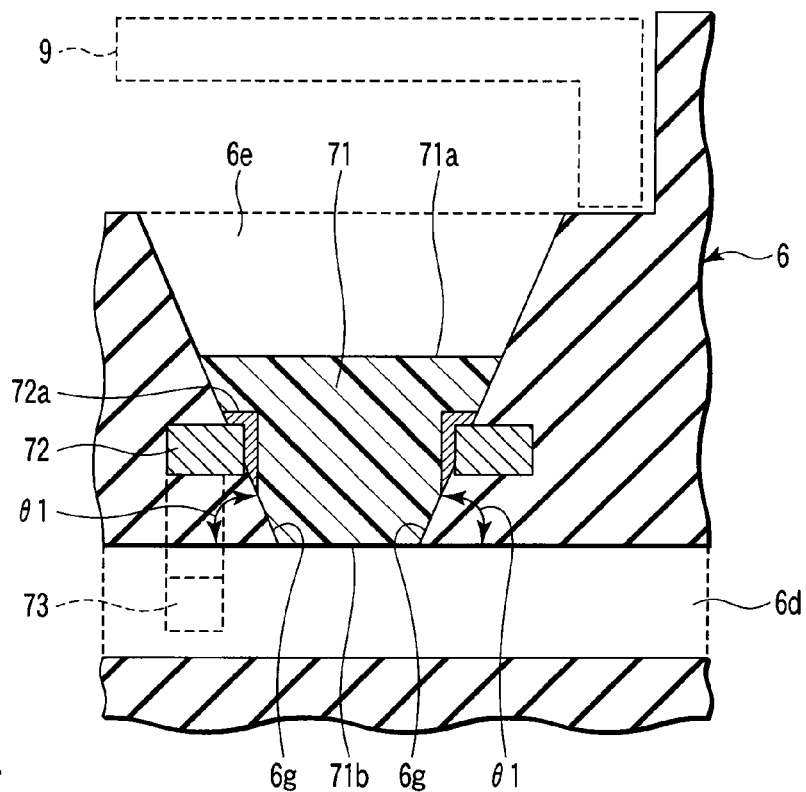
FIG. 4 is an enlarged view of a portion of the multi-ion sensor shown in FIG. 2.
Figure 5:
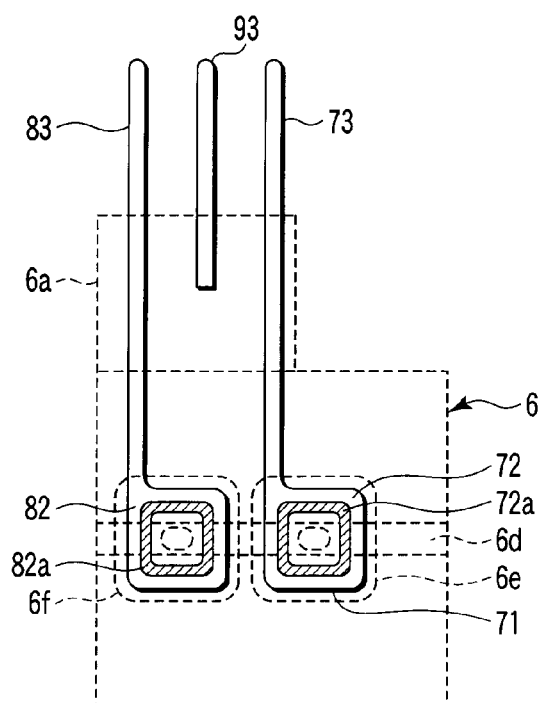
FIG. 5 is a view showing the arrangement of first and second output terminals of the multi-ion sensor shown in FIG. 1.
Figure 6:
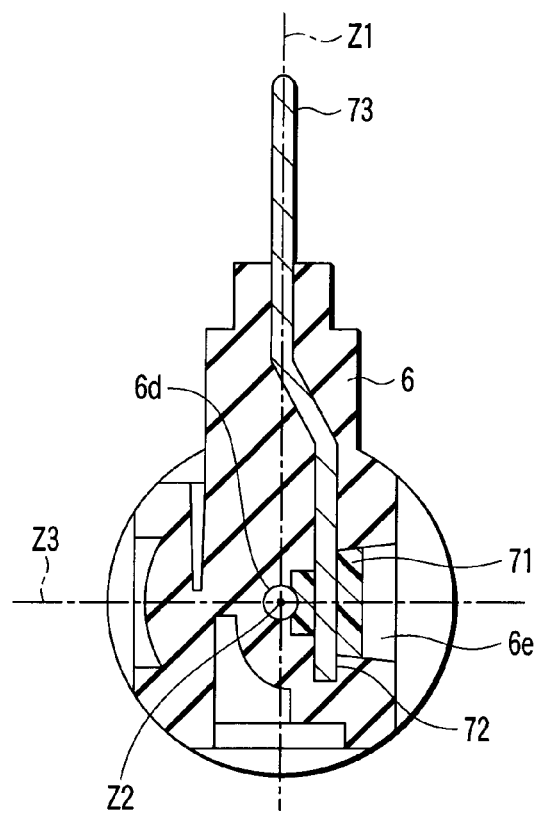
FIG. 6 is a view showing the B-B section of the multi-ion sensor shown in FIG. 1.

The arrangement of the multi-ion sensor 4 will be explained below with reference to FIGS. 1 to 6. FIG. 2 is a view showing the side surface of the multi-ion sensor 4 from which the cover 9 is removed. FIG. 3 is a view showing the A-A section of the multi-ion sensor 4 shown in FIG. 2. FIG. 4 is an enlarged view of a portion of the multi-ion sensor 4 shown in FIG. 3. FIG. 5 is a view showing the arrangement of first and second output terminals of the multi-ion sensor shown in FIG. 1. FIG. 6 is a view showing the B-B section of the multi-ion sensor 4 shown in FIG. 2.

The first sensor main body 6 is made of a material having high electrical insulating properties, e.g., hard vinyl chloride (to be referred to as PVC hereinafter). The first sensor main body 6 has a cylindrical portion, and a first connector 6a formed on the outer surface of the cylindrical portion. The first sensor main body 6 is made of an insulator so that the first and second ion sensors 7 and 8 can be insulated from each other. The first sensor main body 6 has a first cannel 6d extending through the vicinity of the central axis of the cylindrical portion of the first sensor main body 6. A sample flows through the first channel 6d from an upstream surface 6b to a downstream surface 6c of the first sensor main body 6. While the downstream surface 6c is brought into tight contact with the third ion sensor 5 by the container 3, a sample flows from the first channel 6d to the third ion sensor 5.

First and second openings 6e and 6f connected to portions of the first channel 6d are formed in the side surface of the first sensor main body 6 that is rotated almost 90° from the connector 6a around the first channel 6d as the central axis.

The first opening 6e is formed near the upstream surface 6b of the first sensor main body 6. As shown in FIG. 4, the side surfaces of the first opening 6e are inclined surfaces 6g ($0<\theta 1<90°$) that decrease the opening area from the side surface of the first sensor main body 6 toward the first channel 6d. In other words, the first opening 6e has a conical shape whose opening narrows toward the first channel 6d.

The second opening 6f is formed near the downstream surface 6c of the first sensor main body 6 and apart from the first opening 6e. Similarly to the first opening 6e, the wall surfaces of the second opening 6e are inclined surfaces ($0<\theta 1<90°$) that decrease the opening area from the side surface of the first sensor main body 6 toward the first channel 6d.

The first ion sensor 7 has a first responsive portion 71, first electrode 72, and first output terminal 73.

The first responsive portion 71 is filled in the first opening 6e. The surface of the first responsive portion 71 that opposes the cover 9 is called a front surface 71a, and the surface on the side of the channel 6d is called a rear surface 71b. The inclined surfaces 6g make the area of the front surface 71a larger than that of the rear surface 71b. The first responsive portion 71 is made of, e.g., a crown ether-based first responsive material which selectively responds to a first ion such as a sodium ion, and PVC or the like surrounding the first responsive material. As shown in FIG. 4, the rear surface 71b of the first responsive portion 71 forms a part of the wall surface of the first channel 6d. That is, the first responsive portion 71 closes a portion where the first channel 6d and first opening 6e are connected. The boundaries between the rear surface 71b and the inclined surfaces of the first opening 6e are smooth flat surfaces. Also, the inclined surfaces 6g of the first opening 6e hold the side surfaces of the first responsive portion 71.

The cover 9 is detachably attached to the first sensor main body 6. When the cover 9 is unattached to the first sensor main body 6, the first responsive portion 71 filled in the first opening 6e can be observed.

As shown in FIG. 5, the first electrode 72 has a ring shape. The inner circumferential surface of the first electrode 72 is positioned outside the inclined surfaces 6g of the first opening 6e. That is, the first electrode 72 is in partial contact with the first responsive portion 71. Silver chloride is formed in a contact portion 72a on the surface the first electrode 72, which is in contact with the first responsive portion 71. The first electrode 72 having this structure senses the response of the first responsive portion 71 to the first ion. Also, connecting the first responsive portion 71 to the first electrode 72 obviates the need for an internal solution necessary in the conventional apparatus. Accordingly, the first ion sensor 7 can be miniaturized.

The first output terminal 73 has a pin shape extending from the first electrode 72. One end portion of the first output terminal 73 is exposed outside the connector 6a, and connected to an external apparatus such as an electrolyte measuring apparatus. As shown in FIG. 6, let Z1 be the axis of one end portion of the first output terminal 73. A portion of the first output terminal 73 is bent so that the axis Z1 and a central axis Z2 of the first channel 6d perpendicularly cross each other. That is, the axis Z1 is almost perpendicular to the central axis Z2 and a central axis Z3 of the first electrode 72. The first output terminal 73 outputs a potential generated by the first responsive portion 71 having responded to the first ion contained in a sample flowing into the first channel 6d, to the electrolyte measuring apparatus via the first electrode 72. Note that the positional relationship between the first channel 6d, first electrode 72, and first output terminal 73 is not limited to the one described above. For example, the first output terminal 73 may also extend straight from the first electrode 72. That is, the axis Z1 of the first output terminal 73 and the central axis Z2 of the first channel 6d need not cross each other.

The first electrode 72 and first output terminal 73 are formed out of one metal plate. That is, the first electrode 72 and first output terminal 73 are integrally formed by punching from one metal plate.

The second ion sensor 8 is placed in the first sensor main body 6 apart from the first ion sensor 7. The second ion sensor 8 has a second responsive portion 81, second electrode 82, and second output terminal 83. Although these components of the second ion sensor 8 will be explained below, the second responsive portion 81, second electrode 82, and second output terminal 83 respectively have almost the same arrangements as those of the first responsive portion 71, first electrode 72, and first output terminal 73. In addition, the positional relationship between the components of the second ion sensor 8 is almost the same as that between the components of the first ion sensor 7. Accordingly, only differences from the first ion sensor will be explained, and a repetitive explanation will be omitted.

The second responsive portion 81 is filled in the second opening 6f. The second responsive portion 81 is made of, e.g., a crown ether-based second responsive material which selectively responds to a second ion such as a potassium ion, and PVC or the like surrounding the second responsive material. The second electrode 82 senses the response of the second responsive portion 81 to the second ion. The second output terminal 83 outputs the potential of the second responsive portion 81 having responded to the second ion contained in a sample or the like flowing into the first channel 6d of the first sensor main body 6, to the electrolyte measuring apparatus via the second internal electrode 82a.

As shown in FIGS. 2 and 5, the first connector 6a has a dummy output terminal 93 between the first and second output terminals 73 and 83 for the reason explained below. The first connector 6a normally has three holes for receiving output terminals. However, only two output terminals (the first and second output terminals 73 and 83) are inserted into the first sensor main body 6, so one hole is left unused. The dummy output terminal 93 is inserted to fill this extra hole. The dummy output terminal 93 is neither integrated with nor connected to an electrode.

The cover 9 prevents a liquid, high-humidity gas, or the like from entering the first and second openings 6e and 6f of the first sensor main body 6 from outside the ion sensor module 10, thereby preventing a decrease in electrical insulation between the first and second responsive portions 71 and 81 of the first ion sensor 7.

As described above, since the first and second ion sensors 7 and 8 are formed in a single sensor main body (the first sensor main body 6), there is no connecting portion between the first and second ion sensors 7 and 8. Therefore, a single smooth sample flow path (the first channel 6d) related to the first and second ion sensors 7 and 8 can be formed in the first sensor main body 6. Also, the parts cost can be reduced because the first and second ion sensors 7 and 8 are formed in a single sensor main body (the first sensor main body 6).

Note that it is also possible to further form a third opening in the first sensor main body 6, and form a fourth ion sensor by filling the third opening with a fourth responsive portion which selectively responds to a fourth ion. Furthermore, if miniaturization is unnecessary, it is also possible to arrange the first and second electrodes 72 and 82 above the surfaces of the first and second responsive portions 71 and 81, respectively, and fill an internal solution containing an electrolyte in portions between the first and second electrodes 72 and 82 and the first and second responsive portions 71 and 81.

Figure 7:
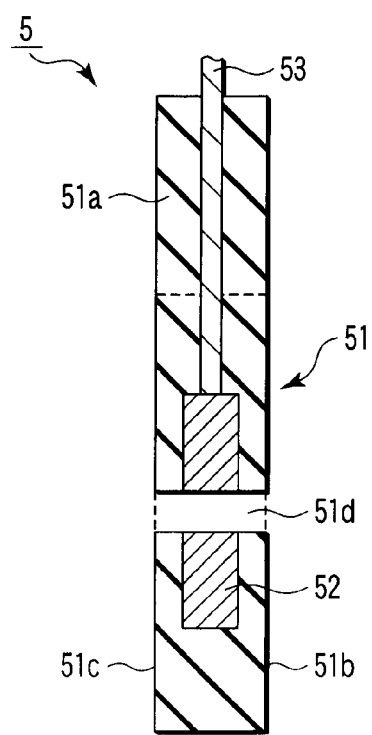
FIG. 7 is a view showing the section of a third ion sensor shown in FIG. 1.

The arrangement of the third ion sensor 5 of the ion sensor unit 1 will be explained with reference to FIG. 7. FIG. 7 is a view showing the section of the third ion sensor 5. The third ion sensor 5 has a second sensor main body 51, third responsive portion 52, and third output terminal 53.

The second sensor main body 51 is made of, e.g., PVC having high electrical insulating properties, and has a cylindrical portion and a second connector 51a formed on the outer surface of the cylindrical portion. The second sensor main body 51 has a second channel 51d extending through the vicinities of the centers of an upstream surface 51b and downstream surface 51c of the cylindrical portion of the second sensor main body 51. The container 3 brings the upstream surface 51b of the second sensor main body into tight contact with the downstream surface 6c of the first sensor main body 6, and brings the downstream surface 51c of the second sensor main body into tight contact with the reference electrode 2. In this state, a sample passing through the first channel 6d flows through the second channel 51d from the upstream surface 51b to the downstream surface 51c of the second sensor main body 51, and flows into the reference electrode 2.

The second sensor main body 51 holds the third responsive portion 52. The third responsive portion 52 is made of, e.g., a third responsive material which selectively responds to a third ion such as a chlorine ion. When the third ion is a chlorine ion, the third responsive portion 52 is formed by press-molding a mixture containing silver chloride or the like. This press-molded mixture, i.e., the third responsive portion 52 has a cylindrical shape. A hole extending through the vicinity of the central axis of the third responsive portion 52 forms a part of the second channel 51d.

One end portion of the third output terminal 53 is connected to the side surface of the third responsive portion 52. The second sensor main body 51 holds a portion of the third output terminal 53. The third output terminal 53 is set parallel to the second output terminal 82 of the second ion sensor 8. The other end portion of the third output terminal 53 is connected to the electrolyte measuring apparatus. The third output terminal 53 outputs the potential of the third responsive portion 52 having responded to the third ion contained in a sample or the like flowing into the second channel 51d, to the electrolyte measuring apparatus. Note that the third output terminal 53 is set perpendicularly to the second channel 51d.

The upstream surface of the connector 51a has the same size as that of the downstream surface of the connector 6a of the first sensor main body 6. Also, the upstream surface 51b has the same size as that of the downstream surface 6c. In addition, the section of the hole of the second channel 51d has the same size as that of the section of the hole of the first channel 6d. The container 3 brings the upstream surface 51b of the second sensor main body 51 and the upstream surface of the connector 51a into tight contact with the downstream surface 6c of the first sensor main body 6 and the downstream surface of the connector 6a, respectively. The container 3 also brings the upstream surface 51b of the second sensor main body 51 into tight contact with the downstream surface 6c of the first sensor main body 6 so as to align the second channel 51d with the first channel 6d. Furthermore, the container 3 urges the downstream surface 51c of the second sensor main body 51 against the reference electrode 2.

Figure 8:
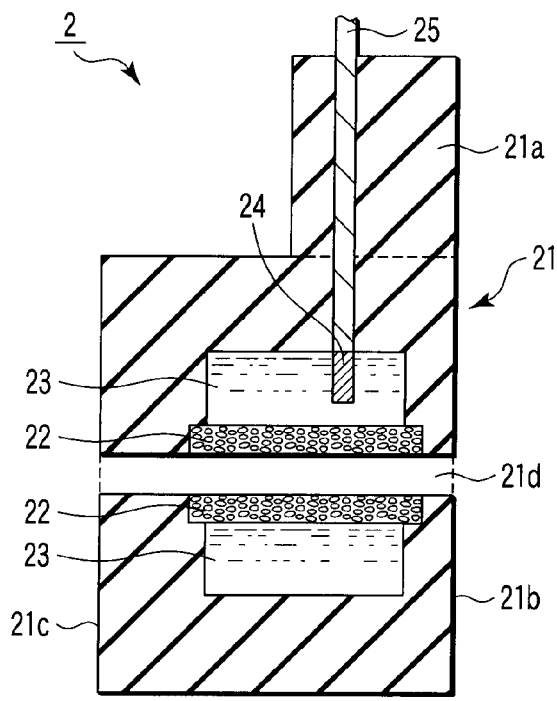
FIG. 8 is a view showing the section of a reference electrode device shown in FIG. 1.

The arrangement of the reference electrode device 2 will be explained below with reference to FIG. 8. FIG. 8 is a view showing the section of the reference electrode device 2. The reference electrode device 2 comprises a reference electrode main body 21, liquid junction hole 22, internal liquid 23, fourth electrode 24, and fourth output terminal 25.

The reference electrode main body 21 is made of, e.g., PVC having high electrical insulating properties, and has a cylindrical portion and a third connector 21a formed on the outer surface of the cylindrical portion. The reference electrode main body 21 has a third channel 21d extending through the vicinities of the centers of an upstream surface 21b and downstream surface 21c, and a recess formed around the third channel 21d. The container 3 brings the upstream surface 21b into tight contact with the downstream surface 51c of the second sensor main body 51 of the third ion sensor 5. In this state, a sample passing through the second channel 51d flows through the third channel 21d from the upstream surface 21b to the downstream surface 21c of the reference electrode main body 21, and is discharged outside.

The upstream surface of the connector 21a has the same size as that of the downstream surface of the second connector 51a of the second sensor main body 51. The upstream surface 21b has the same size as that of the downstream surface 51c of the second sensor main body 51. The section of the hole of the third channel 21d has the same size as that of the section of the hole of the second channel 51d of the second sensor main body 51. The container 3 brings the upstream surface 21b into tight contact with the downstream surface 51c of the second sensor main body 51 so as to align the upstream surface 21b and the upstream surface of the third connector 21a with the second sensor main body 51 and the downstream surface of the second connector 51a, and align the third channel 21d with the second channel 51d.

The reference electrode main body 21 holds the liquid junction hole 22. The liquid junction hole 22 has, e.g., a cylindrical porous structure. The inner surface of the liquid junction hole 22 forms a part of the third channel 21d. The reference electrode main body 21 holds the liquid junction hole 22 except for the inner surface.

The internal liquid 23 contains, e.g., potassium chloride at a high concentration. The internal liquid 23 is contained in the recess of the reference electrode main body 21 so as to be able to communicate, through the liquid junction hole 22, with a sample flowing into the third channel 21d.

The fourth electrode (reference electrode) 24 is made of, e.g., silver/silver chloride, and placed in the recess of the reference electrode main body 21 so as to come in contact with the internal liquid 23.

One end portion of the fourth output terminal 25 is connected to the fourth electrode 24. The other end portion of the fourth output terminal 25 is connected to the electrolyte measuring apparatus outside the third connector 21a of the reference electrode main body 21. The reference electrode main body 21 holds the fourth output terminal 25 such that it is set parallel to the third output terminal 53 of the third ion sensor 5. Note that the reference electrode main body 21 holds the fourth output terminal 25 such that it is perpendicular to the third channel 21d. The fourth output terminal 25 outputs, to the electrolyte measuring apparatus, a predetermined potential of the liquid junction hole 22 that responds to a sample flowing into the third channel 21d of the reference electrode main body 21. This predetermined potential is a reference potential (basic potential) with respect to the potentials sensed by the ion sensors 7, 8, and 5. The electrolyte measuring apparatus calculates the electromotive forces as potential differences between the potentials sensed by the ion sensors 7, 8, and 5 and the reference potential, thereby obtaining the concentrations of the first, second, and third ions in a sample.

Figure 9:
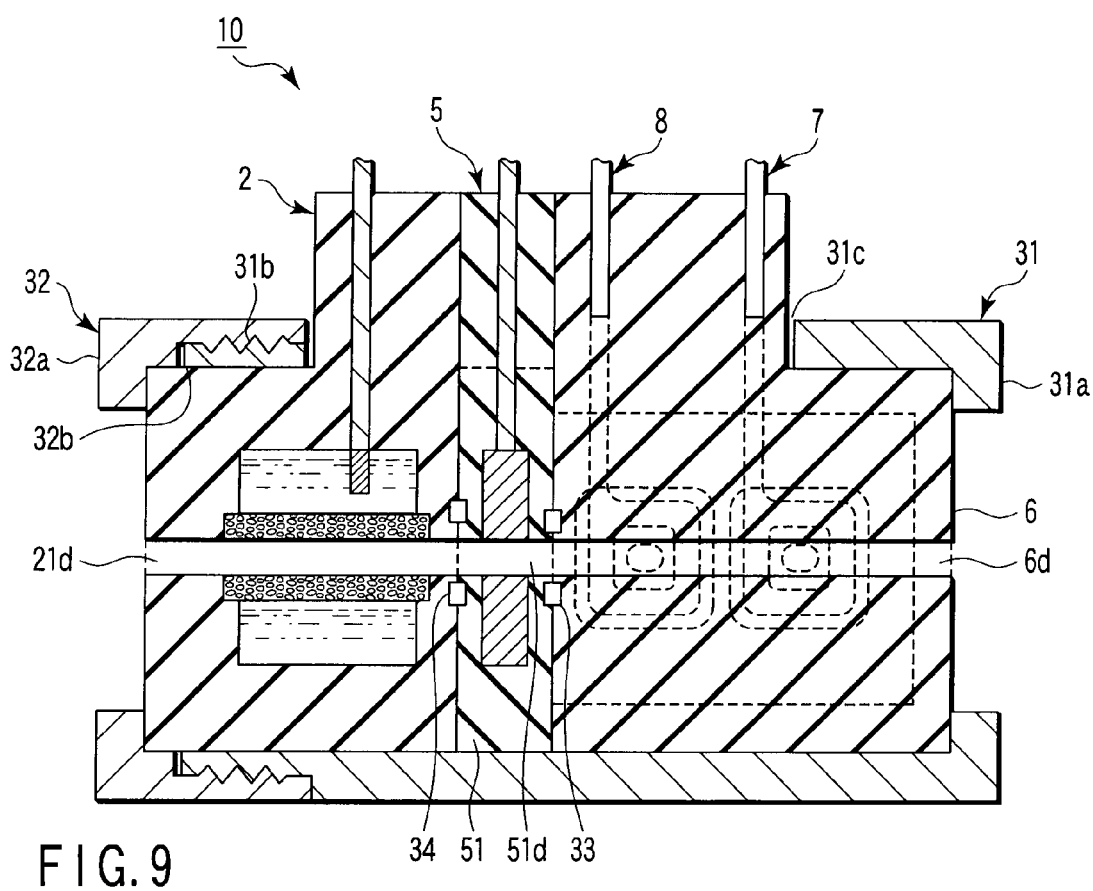
FIG. 9 is a view showing the section of the ion sensor module shown in FIG. 1.

The arrangement of the container 3 will be explained below with reference to FIGS. 1 and 9. FIG. 9 is a view showing the section of the ion sensor module 10.

The container 3 comprises first and second containers 31 and 32 for integrating the multi-ion sensor 4, third ion selective electrode 5, and reference electrode device 2.

The first container 31 has a cylindrical shape. The first container 31 has a bent portion 31a formed by bending one end portion almost perpendicularly toward the central axis. A threaded surface 31b that engages with the second container 32 is formed on the outer surface of the other end portion of the first container 31. A notch 31c is formed in a part of the outer surface of the first container 31. The notch 31c engages with the first connector 6a of the first sensor main body 6 of the multi-ion sensor 4, the second connector 51a of the second sensor main body 51 of the third ion sensor 5, and the third connector 21a of the reference electrode main body 21 of the reference electrode device 2.

The second container 32 has a cylindrical shape, and is shorter than that of the first container 31. The second container has a bent portion 32a formed by bending one end portion almost perpendicularly toward the central axis. The second support member has a threaded surface 32b that is formed on the inner surface of the other end portion. The threaded surface 32b engages with the threaded surface 31b of the first container 31.

A packing 33 is placed between the downstream surface 6c of the first sensor main body 6 and the upstream surface 51b of the second sensor main body 51. More specifically, the packing 33 is placed on the outer surfaces of the first and second channels 6d and 51d between the downstream surface 6c of the first sensor main body 6 and the upstream surface 51b of the second sensor main body 51. A packing 34 is placed between the downstream surface 51c of the second sensor main body 51 and the upstream surface 21b of the reference electrode main body 21. More specifically, the packing 34 is placed on the outer surfaces of the second and third channels 51d and 21d between the downstream surface 51c of the second sensor main body 51 and the upstream surface 21b of the reference electrode main body 21. When urged by the first and second containers 31 and 32, the packing 33 and 34 prevent leakage of a sample flowing into the second channel 51d from the first channel 6d to the outside, and leakage of a sample flowing into the third channel 21*d* from the second channel 51*d* to the outside.

After the multi-ion sensor 4, packing 33, third ion sensor 5, packing 34, and reference electrode device 2 are accommodated into the first container 31 from its opening so that the connectors 6*a*, 51*a*, and 21*a* engage with the notch 31*c*, the second container 32 is engaged with the first container 31. In this manner, the individual components are clamped in the directions of arrows L1 and L2 shown in FIG. 1.

Note that it is also possible to integrate a multi-ion sensor including a fourth ion sensor, the third ion sensor 5, and the reference electrode device 2 by elongating the first container 31. Furthermore, a fifth ion sensor that responds to one specific ion similar to the third ion sensor 5 may also be integrated.

Figure 10:
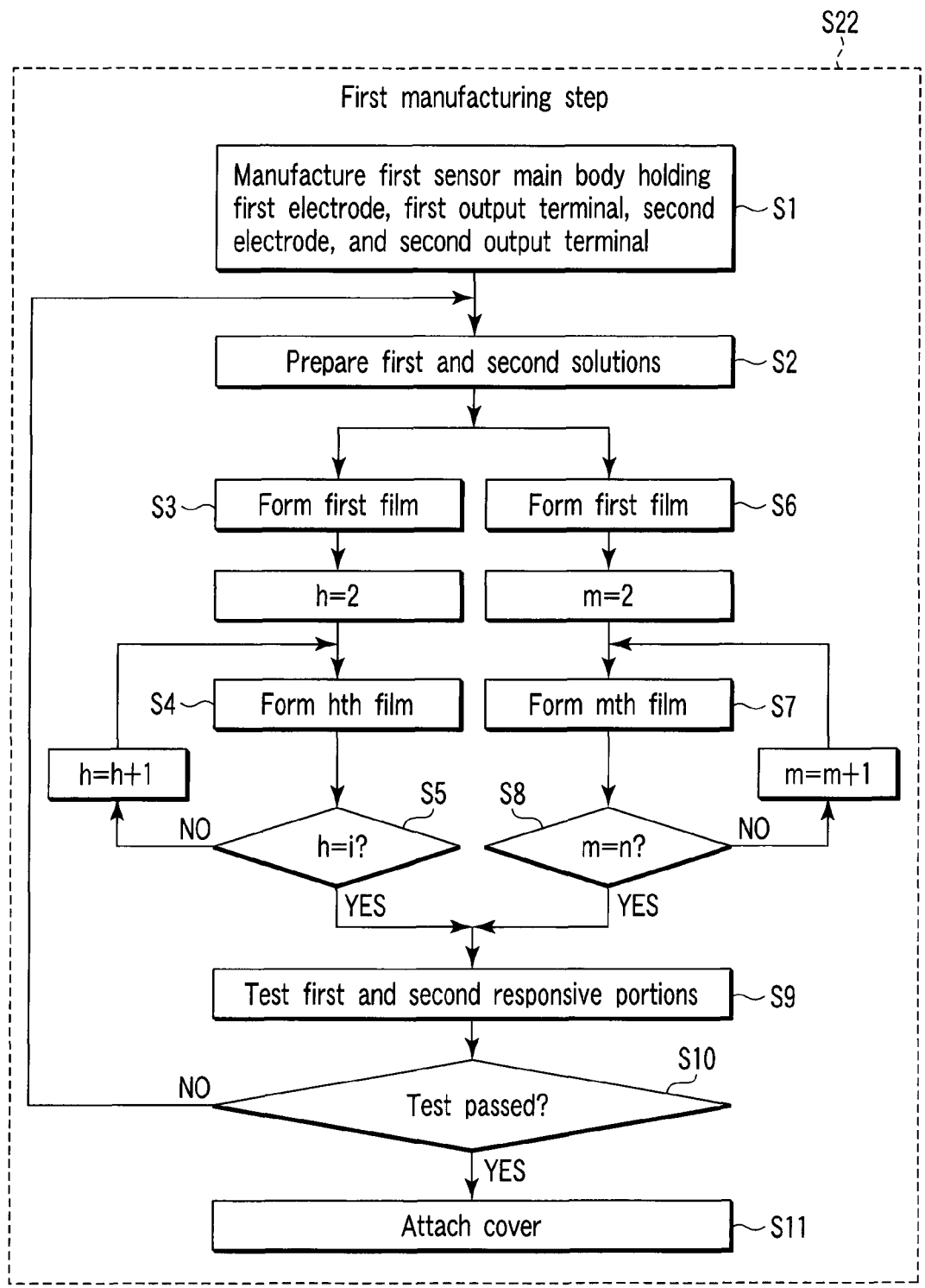
FIG. 10 is a flowchart showing the first manufacturing step according to the embodiment of the present invention.
Figure 11:
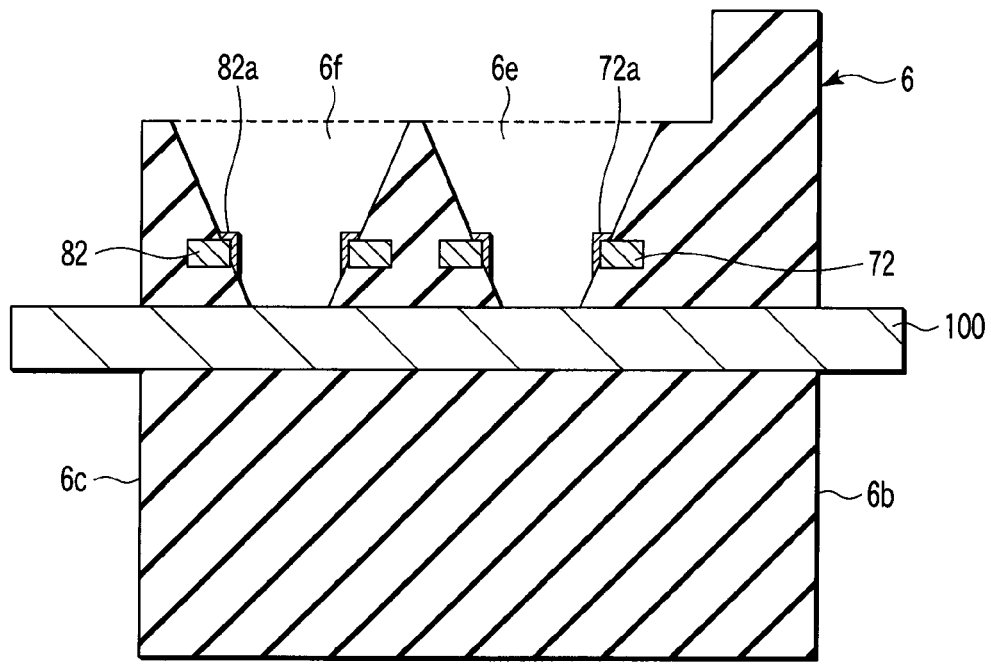
FIG. 11 is a view showing the section of a first sensor main body having a metal pin inserted into a first channel in the first manufacturing step shown in FIG. 10.
Figure 12:
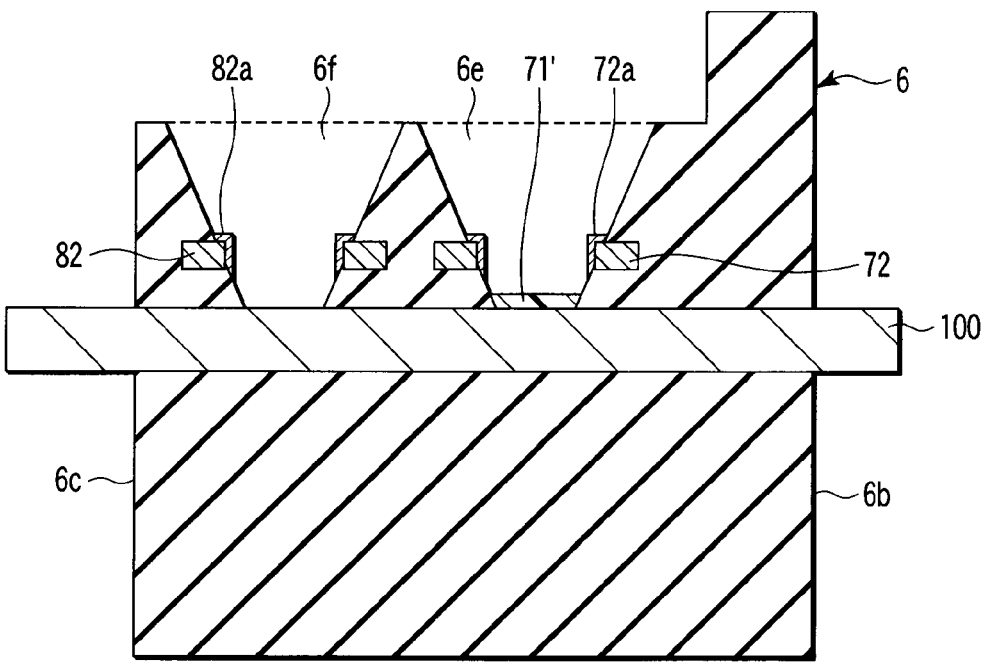
FIG. 12 is a view showing the section of the first sensor main body on which a first film is formed in the first manufacturing step shown in FIG. 10.
Figure 13:
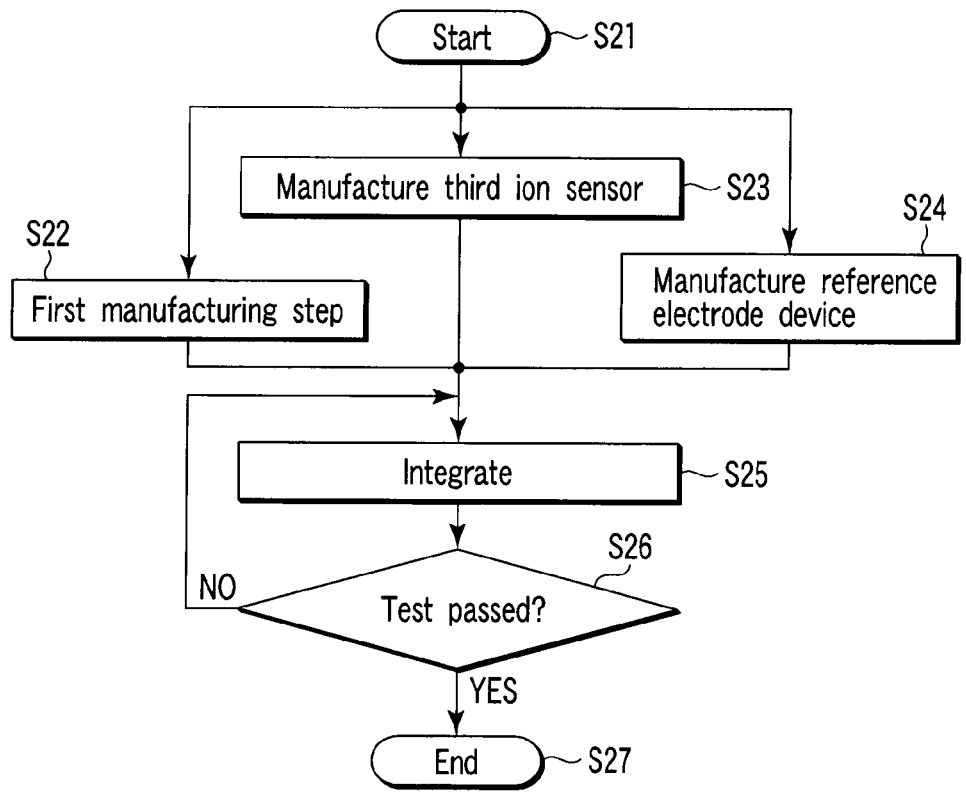
FIG. 13 is a flowchart showing the manufacturing steps of the ion sensor module according to the embodiment of the present invention.
Figure 14:
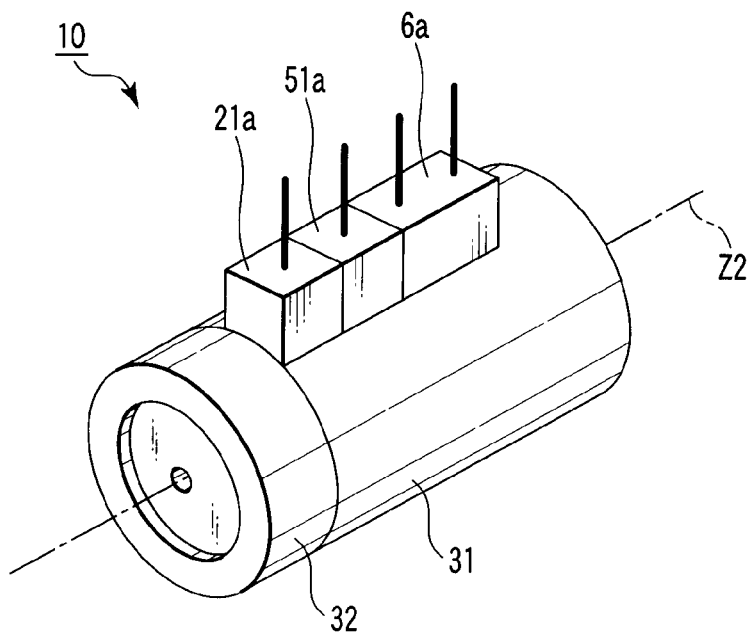
FIG. 14 is a view showing an outline of the ion sensor module according to the embodiment of the present invention.

The manufacturing steps of the ion sensor module 10 will be explained below with reference to FIGS. 1 to 14. FIG. 10 is a flowchart showing the first manufacturing step of manufacturing the multi-ion sensor 4. FIG. 11 is a view showing the section of the first sensor main body 6 in which a metal pin 100 is inserted into the first channel 6*d*. FIG. 12 is a view showing the section of the first sensor main body 6 on which a first film is formed. FIG. 13 is a flowchart showing steps in manufacturing the ion sensor module 10 by using the multi-ion sensor 4 manufactured as shown in FIG. 10. FIG. 14 is a view showing an outline of the ion sensor module 10.

Referring to FIG. 10, first manufacturing step S22 includes steps S1 to S10. First, the first electrode 72, first output terminal 73, second electrode 82, and second output terminal 83 are arranged in predetermined positions of a metal mold. In this state, PVC is poured into the metal mold to perform injection molding, thereby manufacturing the first sensor main body 6 holding the first electrode 72, first output terminal 73, second electrode 82, and second output terminal 83 (step S1).

A first solution is prepared by dissolving the first responsive material, PVC, and the like in a solvent such as tetrahydrofuran (THF). Also, a second solution is prepared by dissolving the second responsive material, PVC, and the like in tetrahydrofuran (THF) (step S2).

After the first and second solutions are thus prepared, as shown in FIG. 11, a metal pin 100 that is made of stainless steel or the like and fits the first channel 6*d* of the first sensor main body 6 with almost no clearance is inserted into the first channel 6*d*. Then, the first sensor main body 6 is positioned such that the first and second output terminals 73 and 83 are set horizontal and the central axes of the first and second electrodes 72 and 82 are set vertical. In other words, the first sensor main body 6 is positioned such that the opening areas of the first and second openings 6*e* and 6*f* increase upward. In this state, the first opening 6*e* is coated with a predetermined amount of the first solution so as to be closed with the solution.

In the first coating, the first solution forms a liquid layer that is almost even over a portion from the metal pin 100 to the inclined surfaces of the first opening 6*e*. When a predetermined time has elapsed from the time of coating, as shown in FIG. 12, THF evaporates from the coated first solution to form a first film thinner than the first liquid layer (step S3). In this state, the side surfaces of the first film are held as they are welded to the inclined surfaces of the first opening 6*e* by THF.

In the hth (h=2) coating, the first solution forms the hth liquid layer that is almost even over a portion from the (h−1)th film to the inclined surfaces of the first opening 6*e*. When a predetermined time has elapsed from the time of coating, THF evaporates from the coated first solution to form the hth film thinner than the hth liquid layer on the (h−1)th film (step S4).

If h=i (YES in step S5), the first responsive portion 71 including the first to ith films is formed in the first opening 6*e*. If h<i (NO in step S5), a film thinner than the first responsive portion 71 is formed in the first opening 6*e*. Therefore, the process returns to step S4 because, e.g., the first electrode 72 and the inclined surfaces of the first opening 6*e* are not connected, the strength of the first responsive portion 71 is insufficient, or the life of the first responsive portion 71 is short. Note that the side surfaces of the first responsive portion 71 are held as they are welded to the inclined surfaces of the first opening 6*e* by THF.

If an air bubble is formed in the coated first solution when THF evaporates in the case that the inclination angle of the inclined surfaces of the first opening 6*e* is 90° or more, this air bubble remains in the first solution because the air bubble cannot rise against the inclined surface. The remaining air bubble forms a pore when the film is formed. If a pore is formed in, e.g., the rear surface 71*b* of the first responsive portion 71 shown in FIG. 4, a sample remains in this pore and contaminates the next sample. This decreases the measurement accuracy of the next sample.

Also, if a large pore is formed near the rear surface 71*b* of the first responsive portion 71, the film thickness of the rear surface 71*b* responsive to the first ion decreases. Therefore, even if the first responsive portion 71 has a performance having passed tests during the manufacture, the life of the first responsive portion 71 is short. In addition, if the total volume of pores formed in the first responsive portion 71 is large, the film resistance increases. This decreases the measurement accuracy of the measurement apparatus because noise of a detection signal in the apparatus increases.

As described above, the metal pin 100 is inserted into the first channel 6*d*, and the first opening 6*e* having the inclined surfaces formed such that the opening area increases upward is coated with the first solution. This makes it possible to form the surface of the first channel 6*d* where the boundary between the rear surface 71*b* of the first responsive portion 71 and the first opening 6*e* is flat and smooth. It is also possible to prevent the formation of a pore in the first responsive portion 71 because an air bubble formed in the first solution rises and releases itself to the atmosphere.

Accordingly, it is possible to prevent the contamination of a sample flowing into the first channel 6*d*, the increase in film resistance, and the decrease in life, and improve the yield and quality of the first ion sensor 7.

In the first coating of the second solution, the second solution forms a first liquid layer that is almost even over a portion from the metal pin 100 to the inclined surfaces of the second opening 6*f*. When a predetermined time has elapsed from the time of coating, THF evaporates from the coated second solution to form a first film thinner than the first liquid layer (step S6).

In the mth (m=2) coating, the second solution forms the mth liquid layer, which is almost even over a portion from the (m−1)th film to the inclined surfaces of the second opening 6*f*. When a predetermined time has elapsed from the time of coating, THF evaporates from the coated second solution to form the mth film, which is thinner than the mth liquid layer, on the (m−1)th film (step S7).

If m=n (YES in step S8), the second responsive portion 81 including the first to nth films is formed in the second opening 6*f*. If m<n (NO in step S8), a film thinner than the second responsive portion 81 is formed in the second opening 6*f*. Therefore, the process returns to step S7 because, e.g., the second electrode 82 and second opening 6f are not connected, the strength of the second responsive portion 81 is insufficient, or the life of the second responsive portion 82 is short.

As described above, the metal pin 100 is inserted into the first channel 6d, and the second opening 6f having the inclined surfaces formed such that the opening area increases upward is coated with the second solution. This makes it possible to form the surface of the first channel 6d where the boundary between one surface of the second responsive portion 81 and the second opening 6f is flat and smooth. It is also possible to prevent the formation of a pore in the second responsive portion 81 because an air bubble formed in the second solution rises and releases itself to the atmosphere.

Accordingly, it is possible to prevent the contamination between samples flowing into the first channel 6d, the increase in film resistance, and the decrease in life, and improve the yield and quality of the second ion sensor 8.

If "YES" in steps S5 and S8, the metal pin 100 is removed from the first sensor main body 6. The first and second responsive portions 71 and 81 are then tested as they are respectively observed from the first and second openings 6e and 6f of the first sensor main body 6 (step S9).

In this manner, the first and second responsive portions 71 and 81 can be respectively observed from the first and second openings 6e and 6f, and hence can be tested when the multi-ion sensor 4 is manufactured.

If the first and second responsive portions 71 and 81 contain no pores (YES in step S10), the first sensor main body 6 having the first and second responsive portions 71 and 81 is regarded as having passed the test. The cover 9 is attached to the first sensor main body 6 having passed the test (step S11). If the first or second responsive portion 71 or 81 contains a pore (NO in step S10), the first sensor main body 6 having the first and second responsive portions 71 and 81 is rejected, and the process returns to step S2.

FIG. 13 is a flowchart showing the manufacturing steps of the ion sensor module 10. First, the manufacture of the ion sensor module 10 is started (step S21).

The multi-ion sensor 4 is manufactured by executing first manufacturing step S22. Also, the second manufacturing step is executed. In the second manufacturing step, the third responsive portion 52 is molded, and the third output terminal 53 is connected to the molded third responsive portion 52. Then, the third responsive portion 52 to which the third output terminal 53 is connected is placed in a predetermined position of, e.g., a metal mold, and PVC is poured into the metal mold to perform injection molding. This step manufactures the third ion sensor 5 including the second sensor main body 51 holding the third responsive portion 52 and third output terminal 53 (step S23).

In the manufacturing step of the reference electrode device 2, the fourth electrode 24 and fourth output terminal 25 are arranged in predetermined positions of a metal mold, and PVC is poured into the metal mold to manufacture the reference electrode main body 21. A portion including, e.g., the upstream surface 21b of the reference electrode main body 21 thus manufactured is notched in order to form the liquid junction hole 22 and receive the internal liquid 23. That is, a recess is formed in the reference electrode main body 21. Subsequently, the liquid junction hole 22 is formed in the reference electrode main body 21, the internal liquid 23 is filled in the recess of the reference electrode main body 21. After that, the notched portion of the upstream surface described above is welded. In this way, the reference electrode 2 including the reference electrode main body 21 holding the liquid junction hole 22, internal liquid 23, fourth electrode 24, and fourth output terminal 25 is manufactured (step S24).

After steps S22, S23, and S24, the container 3 is used to integrate the multi-ion sensor 4, third ion sensor 5, and reference electrode device 2 (step S25).

The integrated multi-ion sensor 4, third ion sensor 5, and reference electrode device 2 are totally tested. If any of the multi-ion sensor 4, third ion sensor 5, and reference electrode device 2 is rejected (NO in step S26), the process returns to step S25. If the multi-ion sensor 4, third ion sensor 5, and reference electrode device 2 have passed the test (YES in step S26), the manufacture of the ion sensor module 10 shown in FIG. 14 is complete, and the process is terminated (step S27).

As described above, the use of the container 3 to which the multi-ion sensor 4, third ion sensor 5, and reference electrode device 2 are detachably attached makes it possible to easily replace a unit found to be defective by the total test with a good one.

It is also possible by the use of the ion sensor module 10 to avoid the trouble of individually attaching the multi-ion sensor 4, third ion sensor 5, and reference electrode device 2 to the electrolyte measuring apparatus. In addition, the decrease in measurement accuracy caused by positional shifts of the channels 6d, 51d, and 21d and packing 33 and 34 when they are attached can be prevented.

In the embodiment of the present invention described above, the metal pin 100 is inserted into the first channel 6d of the first sensor main body 6, and the first and second openings 6e and 6f having a conical shape are respectively coated with the first and second solutions. Therefore, it is possible to form the surface of the first channel 6d where the boundaries between the rear surfaces of the first and second responsive portions 71 and 81 and the first and second openings 6e and 6f are flat and smooth. Furthermore, the formation of a pore in the first and second responsive portions 71 and 81 can be prevented.

This makes it possible to prevent the contamination between samples flowing into the first channel 6d, the increase in film resistance, and the decrease in life, and improve the yield and quality of the first ion sensor 7.

Also, the first and second ion sensors 7 and 8 can be tested when the first and second responsive portions 71 and 81 are formed in the first and second openings 6e and 6f. Accordingly, it is possible to shorten the time of the fabrication steps from the manufacture of the multi-ion sensor 4 to the total test if the first and second responsive portions 71 and 81 are defective.

In addition, since the multi-ion sensor 4, third ion sensor 5, and reference electrode device 2 are detachably attached to the container 3, a unit found to be defective by the total test of the ion sensor module 10 can be replaced with a good one. Consequently, the parts cost and time required to manufacture the ion sensor module 10 can be shortened.

Furthermore, the use of the ion sensor module 10 makes it possible to avoid the trouble of individually attaching the multi-ion sensor 4, third ion sensor 5, and reference electrode device 2 to the electrolyte measuring apparatus. It is also possible to prevent the decrease in measurement accuracy caused by positional shifts of the channels 6d, 51d, and 21d and packing 33 and 34 when they are attached.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ion sensor module comprising:
an ion sensor unit including a sample channel for a sample and configured to selectively respond to a specific ion in the sample;
a reference electrode device including a reference channel for the sample and a liquid junction hole which responds to the sample, and configured to output a substantially constant potential in the liquid junction hole; and
a container housing configured to detachably clamp the ion sensor unit and the reference electrode device to connect the sample channel and the reference channel,
wherein the ion sensor unit and the reference electrode device are longitudinally arranged along a longitudinal axis and slideably disposed within the container housing,
wherein the container housing comprises a first container part having a cylindrical shape and a second container part which engages with the first container part, and the first container and second container parts accommodate the ion sensor unit and the reference electrode device.

2. A module according to claim 1, further comprising a packing placed between the ion sensor unit and the reference electrode device to prevent leakage of the sample.

3. A module according to claim 1, wherein:
the ion sensor unit comprises a sensor main body having the sample channel and an opening connected to the sample channel, a responsive portion which is filled in the opening and selectively responds to a specific ion, and an ion sensor electrode which has a first output terminal and which is embedded in the sensor main body, the ion sensor electrode being partially brought into contact with the responsive portion to sense the response to the specific ion;
the sensor main body comprises a first connector portion through which the first output terminal is extended to protrude from the first connector portion;
the reference electrode device comprises a reference electrode main body having the reference channel, the liquid junction hole formed in the reference channel, an internal liquid contained in the reference electrode main body such that the internal liquid is adapted to communicate with the sample through the liquid junction hole, and a second output terminal which is partially brought into contact with the internal liquid and outputs the substantially constant potential;
the reference electrode main body comprises a second connector portion through which the second output terminal is extended to protrude from the first connector portion;
the first container part includes a slot through which the first and second connector portions extend to provide access to the first and second output terminals.

4. A module according to claim 3, wherein:
the ion sensor electrode includes a portion having in the shape of a ring disposed such that a central axis of the ring is substantially perpendicular to a central axis of the sample channel; and
the first output terminal is formed out of one metal out of which the ion sensor electrode is formed, has a pin shape, and is held by the sensor main body such that an axis of the first output terminal extends along a direction substantially perpendicular to the central axis of the sample channel and to the central axis of the ring.

* * * * *